(12) United States Patent
Kosley, Jr. et al.

(10) Patent No.: US 6,413,986 B1
(45) Date of Patent: Jul. 2, 2002

(54) [1-INDANON-2-YL]METHYLPIPERIDINES

(75) Inventors: Raymond W. Kosley, Jr., Bridgewater; Bettina Spahl, Edison; Richard C. Effland, Bridgewater, all of NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 08/435,079

(22) Filed: May 8, 1995

Related U.S. Application Data

(63) Continuation of application No. 08/118,854, filed on Sep. 10, 1993, now abandoned, which is a continuation of application No. 07/765,279, filed on Sep. 25, 1991, now abandoned.

(51) Int. Cl.$^7$ .................... A61K 31/445; C07D 211/06
(52) U.S. Cl. ........................... 514/319; 546/206
(58) Field of Search ................. 546/206; 514/319

(56) References Cited

U.S. PATENT DOCUMENTS

| | | | | |
|---|---|---|---|---|
| 4,016,281 A | * | 4/1977 | Jonas ........................ | 514/319 |
| 4,091,006 A | * | 5/1978 | Durden ...................... | 514/529 |
| 5,032,598 A | * | 7/1991 | Baldwin .................... | 514/318 |
| 5,071,859 A | * | 12/1991 | Knudsen .................... | 514/326 |
| 5,100,901 A | * | 3/1992 | Sugimoto et al. .......... | 514/319 |

FOREIGN PATENT DOCUMENTS

| EP | 0229319 | 7/1987 |
|---|---|---|
| EP | 0296560 | 12/1988 |

OTHER PUBLICATIONS

Terry et al. "Selected biological activities of novel selenonium choline analogs" Gen. Pharmac. v.23, pp. 689–692, 1992.*
Wilbraham et al. "Organic and Biological chemistry" Benjamin/Cummings Pubs. pp. 268–269, 1984.*
Y. Stern, et al., Neurology, 38, 1837 (1988) published in the United States and entitled "Long-term administration of oral physostigmine in Alzheimer's disease".
R. E. Becker, et al., Drug Development Research, 19, 425 (1990) published in the United States and entitled "Effects of Metrifonate, A Long-Acting Cholinesterase Inhibitor, in Alzheimer's Disease: Report of an Open Trial".

* cited by examiner

*Primary Examiner*—Ceila Chang
(74) *Attorney, Agent, or Firm*—Joseph Strupczewski

(57) ABSTRACT

Novel [[(aminocarbonyloxy)-1-indan]-2-yl]methylpiperidines of the formula

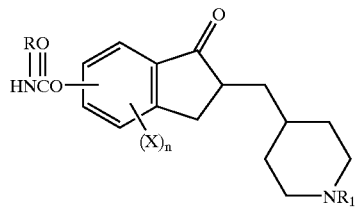

wherein R is hydrogen, loweralkyl, or a group of the formula

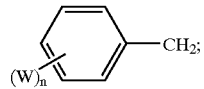

$R_1$ is hydrogen or a group of the formula

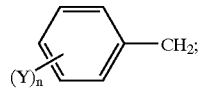

W, X and Y are hydrogen, loweralkyl, loweralkoxy, halogen, nitrogen, or trifluoromethyl; n is 1 or 2; the pharmaceutically acceptable acid addition salts thereof intermediates of the formula

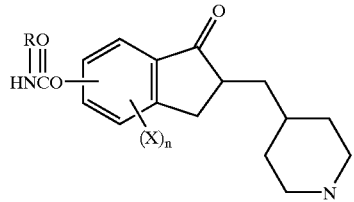

and process for the preparation thereof, and a method of relieving memory dysfunction, employing compounds and compositions thereof are disclosed.

13 Claims, No Drawings

[1-INDANON-2-YL]METHYLPIPERIDINES

This is a continuation, of prior application Ser. No. 08/118,854 filed Sep. 10, 1993, now abandoned, which is a continuation of application Ser. No. 07/765,279 filed Sep. 25, 1991, now abandoned.

The present invention relates to [1-indanon-2-yl]methylpiperidines. More particularly, the present invention relates to [[(aminocarbonyloxy)-1-indanon]-2-yl]methylpiperidines of formula 1

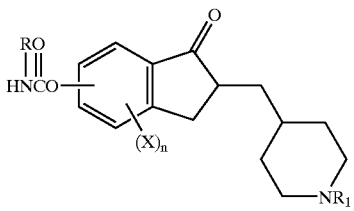

wherein R is hydrogen, loweralkyl, or a group of the formula

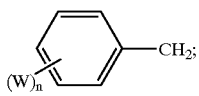

$R_1$ is hydrogen or a group of the formula

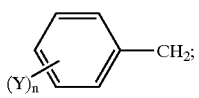

W, X, and Y are hydrogen, loweralkyl, loweralkoxy, halogen, nitro, or trifluoromethyl; n is 1 or 2; the optical isomers thereof; or the pharmaceutically acceptable acid addition salts thereof, which are useful in relieving memory dysfunction, alone or in combination with inert adjuvants, and are thus indicated in the treatment of Alzheimer's disease.

The present invention also relates to 6-(aminocarbonyloxy)-2-[(pyridin-4-yl)methyleneyl]-1-indanones of formula 2

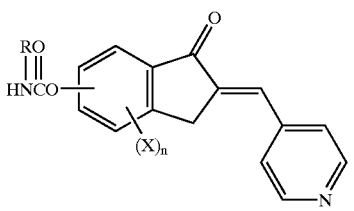

wherein R is hydrogen, loweralkyl, or a group of the formula

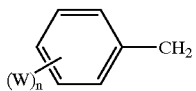

wherein W and X are hydrogen, loweralkyl, loweralkoxy, halogen, nitro, or trifluoromethyl; the optical and geometrical isomers thereof; or pyridine N-oxides thereof, which are useful as intermediates for the synthesis of the present [[(aminocarbonyloxy)-1-indanon]-2-yl]methylpiperidines.

As used throughout the specification and appended claims, the term "alkyl" refers to a straight or branched chain hydrocarbon radical containing no unsaturation and having 1 to 8 carbon atoms. Examples of alkyl groups are methyl, ethyl, 1-propyl, 2-propyl, 1-butyl, 1-pentyl, 3-hexyl, 4-heptyl, 2-octyl and the like. The term "alkoxy" refers to a monovalent substituent which consists of an alkyl group linked through an ether oxygen having its free valence bond from the ether oxygen. Examples of alkoxy groups are methoxy, ethoxy, propoxy, 1-butoxy, 1-pentoxy, 3-hexoxy, 4-heptoxy, 2-octoxy and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid and the like. The term "halogen" refers to a member of the family fluorine, chlorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic group and an optically active acid, or by synthesis from optically active precursors.

The intermediate 2-[(pyridin-4-yl)methylene]-1-indanones of the present invention exist as geometric isomers in which the pyridinyl group is on the same side or the opposite side of the plane of the carbon-to-carbon bond of the methylene function as the carbonyl bearing moiety of the indanone system. In the trans-isomer the pyridinyl group is on the opposite side of the plane containing the carbon-to-carbon double bond, which is perpendicular to the plane of the page, as the carbonyl moiety; in the cis-isomer the pyridinyl group is on the same side.

The 4-[[6-(aminocarbonyloxy)-1-indanon]-2-yl]methylpiperidines of the present invention are prepared by processes illustrated in the Reaction Scheme.

To gain entry into this system, i.e., to prepare an aminocarbonyloxy-indanonylmethylpiperidine 1, a hydroxy-2-[(pyridin-4-yl)methyleneyl]-1-indanone 3, which is described in European Patent Application 0 296 560, published Dec. 28, 1988, is condensed with isocyanic acid or an isocyanate of formula 6

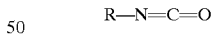

wherein R is hydrogen, loweralkyl, or a group of the formula

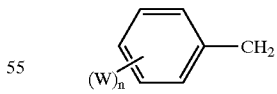

wherein W and n are as hereinbefore described to provide a carbamoyl-2-[(pyridin-4-yl)-methyleneyl]-1-indanone 2, which is reduced to a [[(carbamoyl)-1-indanon]-2-yl]methylpiperidine 4 and, in turn, benzylated to a benzyl [[(carbamoyl)-1-indanon]-2-yl]methylpiperidine 1. The condensation of a carbinol 3 with an isocyanate 6 is performed in a halocarbon solvent with dichloromethane or trichloromethane, trichloromethane being preferred, in the presence of a base, for example, a tertiary amine such as a trialkylamine selected from the group consisting of trimethylamine, triethylamine, and tri-1- or 2-propylamine at an elevated reaction temperature within the range of about 60° to 120° C., in an enclosed system, a reaction bomb, if necessary. A reaction temperature of about 87°–95° C. is preferred.

To prepare a carbamate 2 wherein R is hydrogen, i.e., an N-unsubstituted (aminocarbonyloxy)-2-[(pyridin-4-yl) methyleneyl]-1-indanone 2, a hydroxyindanone 3 may be treated with cyanic acid, generated by and under conditions well-known in the art.

The reduction of a carbamoyl-2[(pyridin-4-yl) methyleneyl]-1-indanone 2 is accomplished by contacting a methyleneylpyridine 2 with hydrogen over a hydrogenation catalyst such as platinum, platinum oxide, palladium, rhodium, or ruthenium, as such, or supported on a material such as carbon, calcium carbonate, or barium carbonate in an alkanoic acid. Included among alkanoic acids are acetic acid and propionic acid. The preferred hydrogenation system consists of platinum oxide and acetic acid. While the pressure and the temperature at which the hydrogenation is conducted are not narrowly critical, it is preferred to conduct the reduction at a hydrogen pressure of from about 1 to about 20 pounds per square inch (psi) and at a temperature from about ambient temperature to about 60° C. A hydrogen pressure of about 20 psi and a reaction temperature of about ambient temperature are preferred.

The benzylation of a (indanon-2-yl)-methylpiperidine 4 is achieved by following conventional methods involving contacting a piperidine 4 with a benzyl halide of formula 7

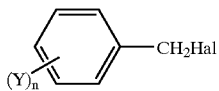

7 wherein Hal is chloro or bromo and Y and n are as hereinbeforedescribed in an alkanone such as, e.g., acetone or 3-butanone in the presence of an acid acceptor such as, e.g., lithium carbonate, potassium carbonate, or sodium carbonate at an alkylation temperature of about ambient temperature. Benzyl bromides and potassium carbonate are the preferred halides and acid acceptor.

Alternatively, a carbamoylindanonylmethylpiperidine 1 is prepared by condensing a [[hydroxy-1-indanon]-2-yl] methylpiperidine 5, which is described in European Patent Application 0 256 506, published Dec. 28, 1988, with isocyanic acid or an isocyanate 6 in an ethereal solvent in the presence of an acid acceptor at a reaction temperature between about 0° C. to about ambient temperature. Among ethereal solvents there may be mentioned diethyl ether, 2-methoxyethyl ether, tetrahydrofuran, or dioxane. Among acid acceptors, there may be mentioned lithium carbonate, potassium carbonate, or sodium carbonate. Tetrahydrofuran and potassium carbonate are the preferred solvent and acid acceptor.

The [1-indanon-2-yl]methylpiperidines of the present invention are useful as agents for the relief of memory dysfunction, particularly dysfunctions associated with decreased cholinergic activity such as those found in Alzheimer's disease. Relief of memory dysfunction activity of the instant compounds is indicated by inhibition of acetyl cholinesterase activity in the assay as described below:

Procedure

A. Reagents
1. 0.05 M Phosphate buffer, pH 7.2
   a) 6.85 g sodium dihydrogen phosphate water/100 ml distilled water
   b) 13.40 g disodium hydrogen phosphate water/100 ml distilled water
   c) add a) to b) until pH reaches 7.2
   d) Dilute 1:10
2. Substrate in buffer
   a) 198 mg acetylthiocholine chloride (10 mM)
   b) q.s. to 100 ml with 0.05 M sodium phosphate, pH 7.2 (reagent 1)
3. DTNB in buffer
   a) 19.8 mg 5,5-dithiobisnitrobenzoic acid (DTNB) (0.5 mM)
   b) q.s. to 100 ml with 0.05 M sodium phosphate, pH 7.2 (reagent 1)
4. A 2 mM stock solution of the test drug is made up in a suitable solvent and q.sed to volume with 0.5 mM DTNB (reagent 3). Drugs are serially diluted (1:10) such that the final concentration (in cuvette) is $10^{-4}$M and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05 M sodium phosphate, pH 7.2 using a Potter-Elvehjem homogenizer. A 25 μl aliquot of this suspension is added to 1 ml of the vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings
Kinetics Soft-Pac Module #598273
Program #6 Kindata:
Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor-1

Reagents are added to the blank and sample cuvettes as follows:
Blank:
0.8 ml phosphate buffer/DTNB
0.8 ml buffer/substrate
Control:
0.8 ml phosphate buffer/DTNB/enzyme
0.8 ml phosphate buffer/substrate
Drug:
0.8 ml phosphate buffer/DTNB/drug/enzyme
0.8 ml phosphate buffer/substrate Blank values are determined for each run to control for non-enzymatic hydrolysis of substrate and these values are automatically subtracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM final concentration % Inhibition=slope control-slope drug/slope control×100

$IC_{50}$ values are calculated from log-probit analysis.

TABLE

| Compound | Acetylcholinesterase Inhibition $IC_{50}$ ($\mu$M) |
|---|---|
| 1-benzyl-4-[(6-methylamino carbonyloxy)-1-indanon]-2-yl] methylpiperidine | 1.343 |
| 1-benzyl-4-[(6-butylaminocarbonyl oxy)-1-indanon]-2-yl]methylpiperidine | 1.43 |
| 1-(3-fluorobenzyl)-4-[(6-methylamino carbonyloxy)-1-indanon]-2-yl] methylpiperidine | 1.508 |
| 1-(3-fluorobenzyl)-4-[(6-benzylamino carbonyloxy)-1-indanon]-2-yl] methylpiperidine | 3.17 |

Compounds of the invention include.

a. 1-benzyl-4-[[(6-aminocarbonyloxy)-1-indanon]-2-yl] methylpiperidine;

b. 4-[[6-methylaminocarbonyloxy)-1-indanon]-2-yl] methylpiperidine;

c. 1-(2-methylbenzyl)-4-[[6-methylaminocarbonyloxy)-1-indanon]-2-yl]methylpiperidine;

d. 1-(3-methoxybenzyl)-4-[[6-methylaminocarbonyloxy)-1-indanon]-2-yl] methylpiperidine;

e. 1-(4-chlorobenzyl)-4-[[6-methylaminocarbonyloxy)-1-indanon]-2-yl]methylpiperidine;

f. 1-(4-trifluoromethyl)-4-[[6-methylaminocarbonyloxy)-1-indanon]-2-yl]methylpiperidine;

g. 1-(3-fluorobenzyl)-4-[[6-(2-methylbenzylamino-carbonyloxy)-1-indanon]-2-yl]methylpiperidine;

h. 1-(3-fluorobenzyl)-4-[[6-(3-methoxybenzylamino-carbonyloxy)-1-indanon]-2-yl]methylpiperidine;

i. 1-(3-fluorobenzyl)-4-[[6-(4chlorobenzylamino-carbonyloxy)-1-indanon]-2-yl]methylpiperidine;

j. 1-(3-fluorobenzyl)-4-[[6-(4-trifluoromethylbenzylamino-carbonyloxy)-1-indanon]-2-yl]methylpiperidine;

k. 1-(3-fluorobenzyl)-4-[[6-(3-methylbenzyl)aminocarbonyloxy)-1-indanon]-2-yl]methylpiperidine;

l. 1-(3-fluorobenzyl)-4-[[6(benzylaminocarbonyloxy)-5-methoxy-1-indanon]-2-yl]methylpiperidine;

m. 1-(3-fluorobenzyl)-4-[[6-(benzylaminocarbonyloxy)-5-chloro-1-indanon]-2-yl]methylpiperidine; and n. 1-(3-fluorobenzyl)-4-[[6-(benzylaminocarbonyloxy)-5-trifluoromethyl-1-indanon]-2-yl]methylpiperidine.

Effective amounts of the compounds of the invention may be administered to a subject by any one of various methods, for example, orally as in capsules or tablets, parenterally in the form of sterile solutions or suspensions, and in some cases intravenously in the form of sterile solutions. The basic final products and intermediates, while effective themselves, may be formulated and administered in the form of their pharmaceutically acceptable acid addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. The preparation should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1-Benzyl-4-[[6-methylaminocarbonyloxy)-1-indanon]-2-yl]methylpiperidine

A suspension of 4-[[6-methylaminocarbonyloxy)-1-indanon]-2-yl]methyleneylpyridine (4.58 g), platinum oxide (0.92 g) and glacial acetic acid (185 ml) was shaken at room temperature at 0–10 psi of hydrogen for 0.5 hr. The pressure was then increased to 20 psi of hydrogen, and the suspension was shaken for 1.25 hr, maintaining the pressure at 20 psi of hydrogen. The suspension was filtered, and the filtrate was concentrated. The residue was dried by azeotroping twice with toluene to provide 4-[[6-methylaminocarbonyloxy)-1-indanon]-2-yl]methylpiperidine.

To 4-[[6-methylaminocarbonyloxy)-1-indanon]-2-yl]methylpiperidine was added milled anhydrous potassium carbonate (12.8 g), 4 angstrom sieve-dried acetone (185 ml) followed by benzyl bromide (1.67 ml), with stirring, under nitrogen. The suspension was stirred at room temperature for 1.25 hr, filtered, and the filtrate was loaded onto a silica gel flash chromatography column (solvent: 4 angstrom sieve-died dichloromethane). The column was eluted with dry dichloromethane, 2% methanol/dichloromethane, and 4% methanol/dichloromethane. The appropriate fractions were combined and concentrated. The residue crystallized on standing. The crystals were dissolved in dry isopropyl alcohol/ethyl acetate and flash chromatographed on silica gel, eluting with ethyl acetate followed by 2% isopropyl alcohoVethyl acetate. The appropriate fractions were combined and concentrated to provide 1.52 g (24.9%) of product, mp 140–142° C.
Analysis

| | | | |
|---|---|---|---|
| Calculated for $C_{24}H_{28}N_2O_3$: | 73.44% C | 7.19% H | 7.14% N |
| Found: | 73.93% C | 7.11% H | 6.99% N |

EXAMPLE 2

1-Benzyl-4-[[6-(butylaminocarbonyloxy)-1-indanon]-2-yl]methylpiperidine

To platinum oxide (2.6 g) and 4-[[6-(butylaminocarbonyloxy)-1-indanon]-2-yl]methyleneyl]pyridine (12.4 g), under argon, was added glacial acetic acid (480 ml). The suspension was shaken at 20 psi of hydrogen for 1.5 hr and filtered. The filtrate was added to platinum oxide (1.6 g), under argon. The suspension was shaken at 20 psi of hydrogen for 40 min, filtered, and the filtrate was concentrated. The residue was dried by azeotroping with dry toluene to provide 4-[[6-(butylaminocarbonyloxy)-1-indanon]-2-yl]methylpiperidine, as an oil. To the oil was added anhydrous potassium carbonate (46.2 g) and dry 2-butanone (480 ml). To this mixture was added dropwise a solution of benzyl bromide (3.62 ml) in dry 2-butanone (120 ml). The mixture was stirred for 1 hr at room temperature, filtered, and the filtrate was flash chromatographed on silica gel, eluting with dry dichloromethane and sequentially, 1%, 2%, 3% methanol/dichloromethane, respectively. The appropriate fractions were combined and concentrated to provided 3.2 g (19.2%) of product. Recrystallization from isopropyl alcohol provided analytically pure product, mp 125–127° C.
Analysis

| | | | |
|---|---|---|---|
| Calculated for $C_{27}H_{34}N_2O_3$: | 74.62% C | 7.89% H | 6.45% N |
| Found: | 74.60% C | 7.80% H | 6.41% N |

EXAMPLE 3

1-(3-Fluorobenzyl)-4-[[6-(methylaminocarbonyloxy)-1-indanon]-2-yl]methylpiperidine To a stirred suspension of 1-(3-fluorobenzyl-4-[[6-hydroxy-1-indanon]-2-yl]methylpiperidine (2.31 g), dry tetrahydrofuran (40 ml), and anhydrous potassium carbonate (1.81 g) was added by syringe methyl isocyanate (0.44 ml), under nitrogen at 0° C. The mixture was stirred at 0° C. for 15 min, allowed to warm to room temperature, and flash chromatographed on silica gel, eluting with chloroform and 1% (dry) methanol/chloroform. The appropriate fractions were combined and concentrated. The other fractions were combined and chromatographed again, employing the same system. The resulting fractions were combined and concentrated. The residues were combined and dried (60°, 2 mm) to provide 1.95 g (72.6%) of product, mp 143–145° C.
Analysis

| | | | |
|---|---|---|---|
| Calculated for $C_{24}H_{27}FN_2O_3$: | 70.22% C | 6.63% H | 6.82% N |
| Found: | 70.01% C | 6.51% H | 6.83% N |

EXAMPLE 4

1-(3-Fluorobenzyl)-4-[[6-(benzylaminocarbonyloxy)-1-indanon]-2-yl]-methylpiperidine To a stir suspension of 1-(3-fluorobenzyl)-4-[[6-hydroxy-1-indanon]-2-yl]methylpiperidine (2.03 g), anhydrous tetrahydrofuran (35 ml), and anhydrous milled potassium carbonate (1.59 g) was added, benzyl isocyanate (0.81 ml) in an ice-bath, by syringe, under nitrogen. The mixture was stirred for 15 min at 0° C., allowed to warm to room temperature, and flash chromatographed on silica gel, eluting with chloroform, 1% methanol/chloroform, and 2% methanol/chloroform The appropriate fractions were combined and concentrated to provide, after drying at 80° (1 mm), 2.32 g (98%) of product.
Analysis

| | | | |
|---|---|---|---|
| Calculated for $C_{30}H_{31}FN_2O_3$: | 74.05% C | 6.42% H | 5.76% N |
| Found: | 74.29% C | 6.45% H | 5.80% N |

REACTION SCHEME

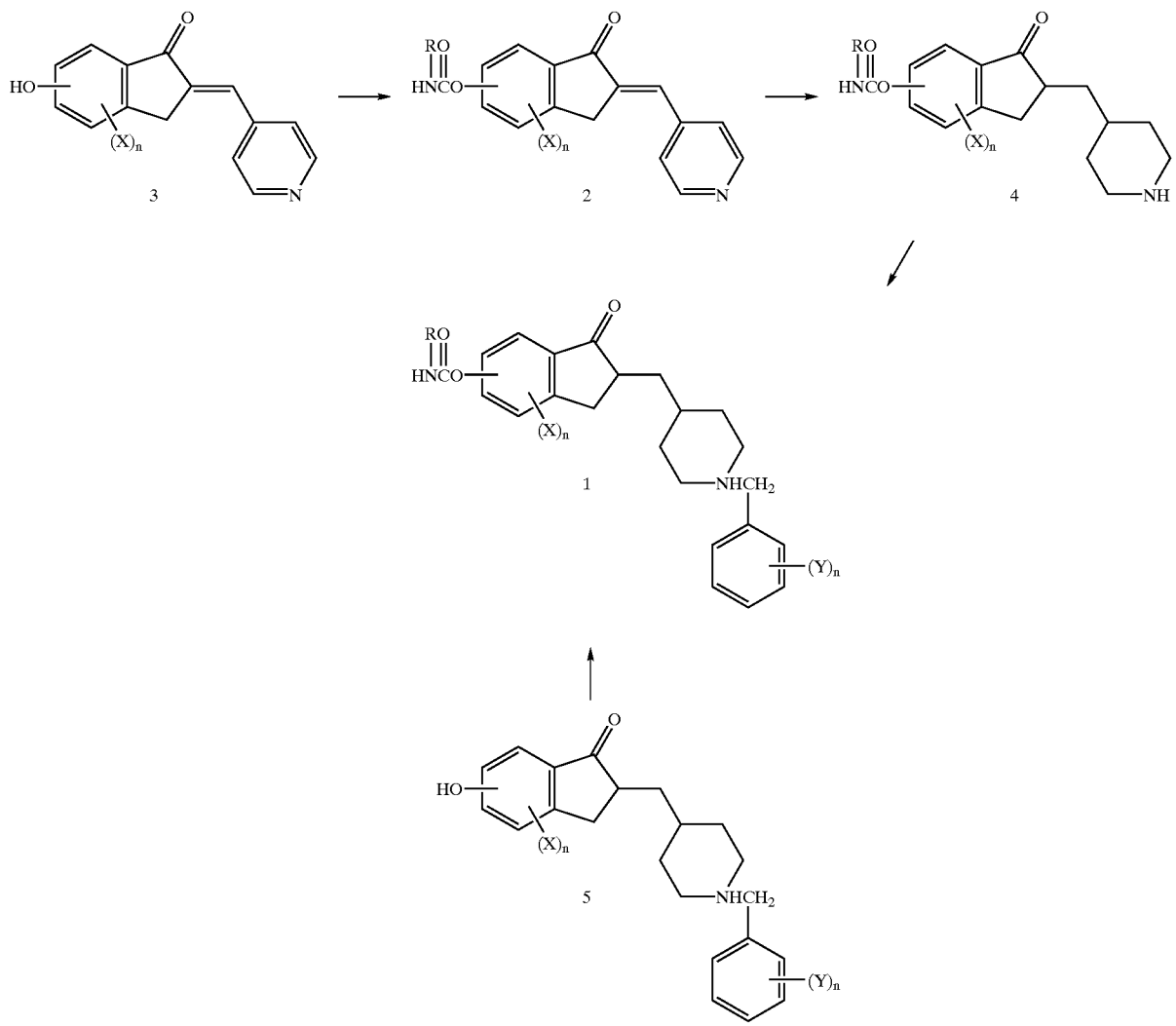

Wherein R, X, Y, and n are as hereinbeforementioned

We claim:
1. A compound of the formula

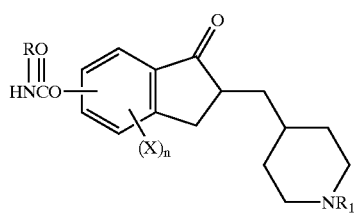

wherein R is hydrogen, loweralkyl, or a group of the formula

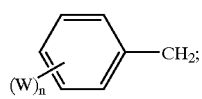

$R_1$ is hydrogen or a group of the formula

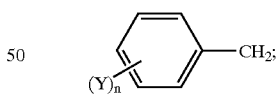

W, x and Y are hydrogen, loweralkyl, loweralkoxy, halogen, nitro or trifluoromethyl; n is 1 or 2; with the proviso, that when n is 1 and X is methoxy, Y is not hydrogen; the optical isomers thereof; or the pharmaceutically acceptable acid addition salts thereof.

2. A compound according to claim 1 which is 4-[[6-(butylaminocarbonyloxy)-1-indanon]-2-yl]methylpiperidine.

3. A compound according to claim 1 which is [[6-(methylaminocarbonyloxy)-1-indanon]-2-yl]methylpiperidine.

4. The compound according to claim 1 which is 1-benzyl-4-[[6-methylaminocarbonyloxy)-1-indanon]-2-yl]methylpiperidine.

5. The compound according to claim 1 which is 1-benzyl-4-[[6-(butylaminocarbonyloxy)-1-indanon]-2-yl]methylpiperidine.

6. The compound according to claim 1 which is 1-(3-fluorobenzyl)-4-[[6-(methylaminocarbonyloxy)-1-indanon]2-yl]methylpiperidine.

7. The compound according to claim 1 which is 1-(3-fluorobenzyl)-4-[[6-(benzylaminocarbonyloxy)-1-indanon]2-yl]methylpiperidine.

8. A compound of the formula

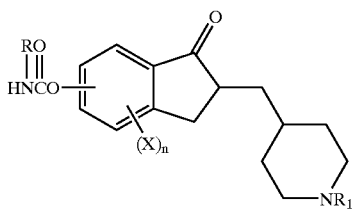

wherein R is hydrogen, loweralkyl, or a group of the formula

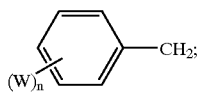

$R_1$ is hydrogen or a group of the formula

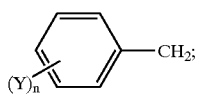

W, X and Y are hydrogen, loweralkyl, halogen, nitro or trifluoromethyl; n is 1 or 2; the optical isomers thereof; or the pharmaceutically acceptable acid addition salts thereof.

9. The compound according to claim 6 which is 6-(methylaminocarbonyloxy)-2-[(pyridine-4-yl)methyleneyl]1-indanone.

10. The compound according to claim 6 which is trans-6-(methylaminocarbonyloxy)-2-[(pyridin-4-yl)methyleneyl]-1-indanone.

11. A method of relieving memory dysfunction in mammals comprising administering to a mammal requiring memory dysfunction relief, a memory dysfunction relieving effective amount of a compound of claim 1.

12. A memory dysfunction relieving composition comprising an adjuvant and as the acetic ingredient, a memory dysfunction relieving effective amount of a compound of claim 1.

13. A compound of the formula

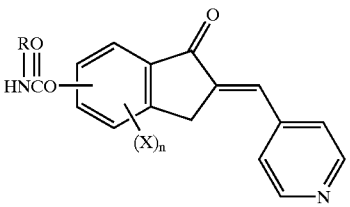

wherein R is hydrogen, loweralkyl, or a group of the formula

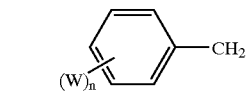

wherein X is hydrogen, loweralkyl, loweralkoxy, halogen, nitro, or trifluoromethyl; the optical and geometrical isomers thereof; or pharmaceutically acceptable salts and pyridine N-oxides thereof.

* * * * *